US00PP11350P

United States Patent [19]

Jepsen

[11] Patent Number: Plant 11,350

[45] Date of Patent: Apr. 18, 2000

[54] KALANCHOE PLANT NAMED 'AFRICAN ORANGE'

[75] Inventor: Knud Jepsen, Hinnerup, Denmark

[73] Assignee: Knud Jepsen A/S, Hinnerup, Denmark

[21] Appl. No.: 09/106,061

[22] Filed: Jun. 29, 1998

[51] Int. Cl.[7] ..... A01H 5/00

[52] U.S. Cl. ..... Plt./340

[58] Field of Search ..... Plt./335, 338, 340

*Primary Examiner*—Howard J. Locker

*Attorney, Agent, or Firm*—C. A. Whealy

[57] ABSTRACT

A distinct cultivar of Kalanchoe plant named 'African Orange', characterized by its numerous and large light orange flowers; dark green serrated and tri-parted leaves; and good postproduction longevity.

2 Drawing Sheets

BACKGROUND OF THE INVENTION

The present invention relates to a new and distinct cultivar of Kalanchoe plant, botanically known as *Kalanchoe hybrida*, and hereinafter referred to by the cultivar name African Orange.

The new Kalanchoe is a product of a planned breeding program conducted by the Inventor in Hinnerup, Denmark. The objective of the breeding program was to create new Kalanchoe cultivars with large flowers, interesting leaf shape, and good postproduction longevity.

The new Kalanchoe originated from a cross made by the Inventor of an unnamed selection of *Kalanchoe laciniata* as the male, or pollen, parent with the *Kalanchoe blossfeldiana* cultivar Anita (not patented) as the female or seed parent. The cultivar African Orange was discovered and selected by the Inventor as a flowering plant within the progeny of the stated cross in a controlled environment in Hinnerup, Denmark.

Asexual reproduction of the new Kalanchoe by terminal cuttings taken at Hinnerup, Denmark, has shown that the unique features of this new Kalanchoe are stable and reproduced true to type in successive generations.

BRIEF SUMMARY OF THE INVENTION

The cultivar African Orange has not been observed under all possible environmental conditions. The phenotype may vary somewhat with variations in environment such as temperature, daylength and light intensity, without however, any variance in genotype.

The following observations, measurements and comparisons describe plants grown in Hinnerup, Denmark, under commercial practice in a glass-covered greenhouse.

The following traits have been repeatedly observed and are determined to be the unique characteristics of 'African Orange'. These characteristics in combination distinguish 'African Orange' as a new and distinct cultivar:

1. Numerous and large light orange flowers.
2. Dark green serrated and tri-parted leaves.
3. Good postproduction longevity.

The new Kalanchoe is most similar to the male parent, the unnamed selection of *Kalanchoe laciniata*. The new Kalanchoe differs from plants of the unnamed selection of *Kalanchoe laciniata* in flower color, thickness of the leaves and healthier lower foliage.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type. The photographs were taken under diffuse natural light conditions on an overcast day with electronic flash at approximately noon in Hinnerup, Denmark.

The photograph on the first sheet comprises a side perspective view of a typical potted plant of 'African Orange'.

The photograph at the top of the second sheet comprises a top perspective view of a typical potted plant of 'African Orange' showing the flowers and foliage.

The photograph at the bottom of the second sheet is a close-up view of the following (from left to right): side perspective view of a typical flowering cyme; top perspective view of a typical flowering cyme; and immature (top) and fully expanded leaves (bottom). Flower and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used.

Botanical classification: *Kalanchoe hybrida* cultivar African Orange.

Parentage:

*Male or pollen parent.*—Unnamed selection of *Kalanchoe laciniata*

*Female or seed parent.*—*Kalanchoe blossfeldiana* cultivar Anita (not patented).

Propagation:

*Type cutting.*—Terminal cuttings.

*Time to initiate roots.*—About 14 days.

*Rooting habit.*—Numerous, fine, fibrous, and well-branched.

Plant description:

*Form.*—Upright and tall; plant shape is columnar or triangular. Actual plant shape will depend on whether or not plants are pinched (apical terminals removed). Long internodes, long and upright flowering stems. Appropriate for 13—cm containers with one cutting per container.

*Branching habit.*—Freely branching. Pinching (removal of terminal apex) is recommended during winter production to promote branching.

*Plant height at flowering.*—About 38 cm.

*Plant diameter at flowering.*—About 35 cm.

*Foliage description.*—Leaves simple, opposite, generally symmetrical, tri-parted. Size: Leaf size is reduced after floral induction. Vegetative plants: Length: About 20 cm. Width: About 15 cm. Reproductive plants: Length: About 8 cm. Width: About 4 cm. Shape: Roughly hastate. Apex: Obtuse. Base: Cuneate. Margin. Serrated. Texture: Leathery, glabrous, and succulent. Color: Young foliage upper side: 137A. Young foliage under side: 137C. Mature foliage upper side: 137A. Mature foliage under side: 137C.

Flower description:

*Flower type and habit.*—Single flowers arranged in compound dichasial cymes. The main inflorescence is branched into one primary and two to four minor cymes during development. Freely flowering. Flowers persistent.

*Natural flowering season.*—Late autumn/winter/early spring; flower initiation and development can be induced under short day/long night conditions.

*Inflorescences borne.*—Above foliage, arising from leaf axils.

*Time to flower.*—In the summer with 20° C. growing temperatures, about 13.5 weeks of short day/long night conditions are required to produce flowering plants. During the winter with supplemental lighting and 20° C. growing temperatures, about 15.5 weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About 1.5 weeks after the first flower has opened, 50% of the remaining flowers are open.

*Flower diameter.*—About 2.1 cm.

*Quantity.*—On unpinched plants, at least 150 flower per plant.

*Flower buds.*—Shape: Narrowly oblong. Length: About 1.8 cm. Width: About 4 mm. Color: 22A.

*Petals.*—Quantity: Four fused at base to form bell-shaped corolla. Length: About 9 mm. Shape: Round obovate. Apex: Cuspidate. Margin: Entire. Texture: Glabrous, smooth and satiny. Color: Mature, upper side: 25A. Mature, under side: 22A.

*Reproductive organs.*—Stamens: Stamen number: Eight. Anther shape: Slightly oblong. Filament color: Yellow green. Pollen color: Yellow. Pistils: Pistil number: Four. Style color: White. Stigma shape: Round. Ovaries: Hypogenous and four-celled. Ovary size: 6 mm by 2 mm. Ovary color: Light green.

Disease resistance: Resistance to known Kalanchoe diseases has not been observed to date under commercial practice.

Seed production: Seed production has not been observed.

It is claimed:

1. A new and distinct cultivar of Kalanchoe plant named 'African Orange', as illustrated and described.

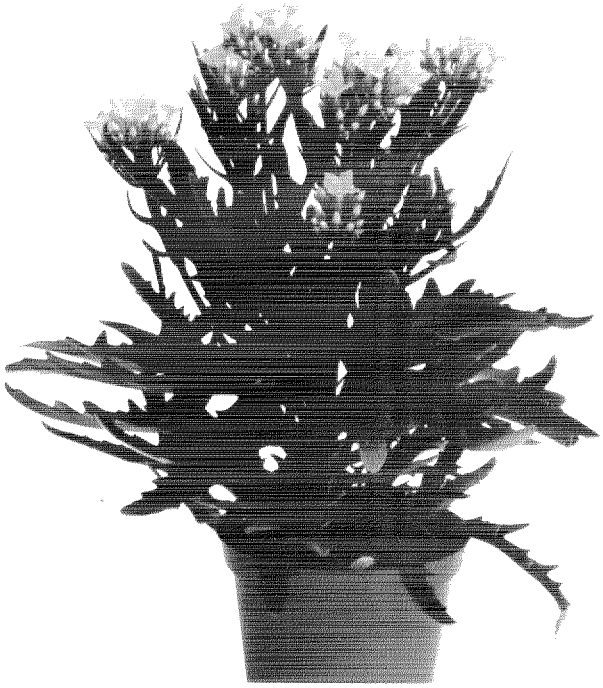

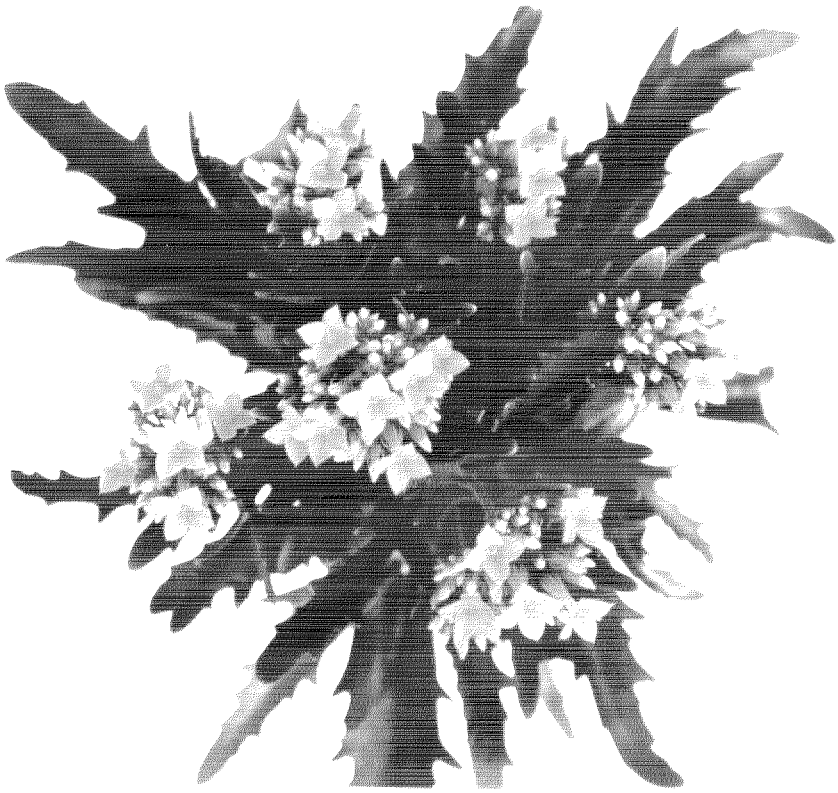
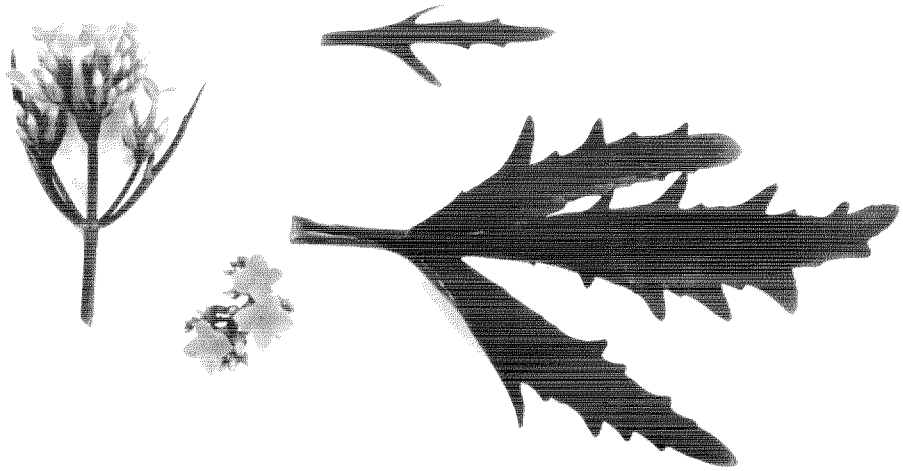

* * * * *